United States Patent [19]
Bretton

[11] Patent Number: 6,106,554
[45] Date of Patent: Aug. 22, 2000

[54] INTRAOCULAR LENS IMPLANTS FOR THE PREVENTION OF SECONDARY CATARACTS

[75] Inventor: Randolph H. Bretton, Belleville, Ill.

[73] Assignee: Bausch & Lomb Surgical, Inc., Claremont, Calif.

[21] Appl. No.: 09/257,678

[22] Filed: Feb. 25, 1999

[51] Int. Cl.[7] ........................................................ A61F 2/16
[52] U.S. Cl. ........................ 623/6.62; 623/6.56; 128/898
[58] Field of Search ................................ 623/6.56, 6.62, 623/6.16, 6.11; 128/898; 530/391.7, 391.9; 424/422, 423, 426, 427; 514/2, 8, 23

[56] References Cited

U.S. PATENT DOCUMENTS

| | | | |
|---|---|---|---|
| 4,432,751 | 2/1984 | Emery et al. | 604/49 |
| 4,515,794 | 5/1985 | Emery et al. | 514/249 |
| 4,657,930 | 4/1987 | Emery et al. | 514/557 |
| 4,847,240 | 7/1989 | Ryser et al. | 514/12 |
| 4,871,350 | 10/1989 | Lam et al. | 604/49 |
| 4,918,165 | 4/1990 | Soll et al. | 530/391 |
| 5,055,291 | 10/1991 | Lam et al. | 424/85.91 |
| 5,202,252 | 4/1993 | Emery et al. | 435/240.27 |
| 5,273,751 | 12/1993 | Dubroff | 424/427 |
| 5,620,013 | 4/1997 | Bretton | 128/898 |

*Primary Examiner*—Dinh X. Nguyen
*Attorney, Agent, or Firm*—Rita D. Vacca

[57] ABSTRACT

A surface treated intraocular lens implant for use in the replacement of a cataracts natural lens to prevent posterior cellular opacification. The surface treated intraocular lens includes one or more carbohydrates covalently bound to the surface of the intraocular lens implant and a carbohydrate binding agent conjugated to a cytotoxic agent for binding said carbohydrates. The cytotoxic agent present on the intraocular lens implant serves to destroy residual lens epithelial cells within the lens capsule thereby preventing posterior cellular opacification of the intraocular lens implant.

51 Claims, No Drawings

INTRAOCULAR LENS IMPLANTS FOR THE PREVENTION OF SECONDARY CATARACTS

FIELD OF THE INVENTION

The present invention relates to surface treated intraocular lens implants, a method of surface treating intraocular lens implants and a method of using surface treated intraocular lens implants to destroy residual lens epithelial cells for the purpose of preventing lens epithelial cell proliferation and posterior capsule opacification (PCO) or secondary cataract formation following the extracapsular extraction of a cataractous lens. More particularly, the present invention is directed to intraocular lens implant chemically bound with a toxin conjugate for specific destruction of epithelial cells on the interior surface of the lens capsule of the eye.

BACKGROUND OF THE INVENTION

Cataract extraction is among the most commonly performed operations in the United States and the world. A cataractous lens is located within a capsular sac or lens capsule in the posterior chamber of the eye. In order to gain access to the cataractous lens, an incision typically is made at the limbus of the eye for the purpose of introducing a surgical instrument into the anterior chamber of the eye. In the case of extracapsular cataract extraction, a capsularhexis procedure is performed in which a portion of the anterior membrane of the lens capsule adjacent to the iris is removed using a surgical cutting instrument in order to provide direct access to the cataractous lens from the anterior chamber. The diseased lens is then removed through various known methods, including phacoemulsification. Phacoemulsification is a procedure entailing the application of ultrasonic energy to the diseased lens in order to break the cataractous lens into small pieces that can be aspirated from the lens capsule. With the exception of the portion of the anterior membrane of the lens capsule removed during the capsularhexis procedure, the lens capsule remains substantially intact throughout an extracapsular cataract extraction. Following removal of the cataractous lens, an artificial intraocular lens (IOL) implant is typically implanted within the lens capsule in order to mimic the refractive function of the lens.

Although cataractous lens removal with IOL implant replacement provides significant benefits to most cataract patients, it is estimated that up to fifty percent (50%) of all patients who have IOL implants placed within the lens capsule will develop posterior capsular opacification (PCO) or secondary cataracts within five years after surgery. PCO is caused by the deposit of cells and fibers on the IOL implant and on the posterior capsular membrane, thereby obstructing light passing through the IOL implant and obscuring the patient's vision. These cell deposits originate from two sources: (1) the proliferation of residual lens epithelial cells on the interior surface of the lens capsule after surgery; and (2) the accumulation of inflammatory cells and protein deposits on the intraocular lens implant. Of these two sources, the major cause of PCO by far is the proliferation and migration of the residual lens epithelial cells on the capsular membrane.

Ophthalmic surgeons, aware of the problems associated with residual lens epithelial cells, typically take considerable care in trying to remove all residual lens epithelial cells prior to the implantation of an artificial IOL implant. However, despite these efforts, a significant number of lens epithelial cells usually are left on the interior surface of the lens capsule due to the fact that these cells are difficult to identify and are often difficult to reach due to their position on the inside surface of the lens capsule.

The most common treatment for PCO entails the application of laser energy to the posterior membrane of the lens capsule for the purpose of destroying the lens epithelial cells propagating thereon. However, the laser energy applied to the posterior membrane of the lens capsule is ordinarily directed through the IOL implant possibly resulting in damage to the optical and/or structural characteristics of the IOL implant. The application of laser energy to the posterior membrane of the lens capsule also typically results in the destruction of a portion of the lens capsule as well as the residual lens epithelial cells propagating thereon. The destruction of a portion of the lens capsule creates a risk of exposure to the vitreous, possibly resulting in serious or irreparable damage to the eye. In addition, the destruction of a portion of the lens capsule creates a risk of shrinkage of the lens capsule, which may result in a compromise in the optical characteristics of the IOL implant. In certain cases, the destroyed posterior capsular tissue may also regenerate, e.g., as a result of a fibrin clot. Accordingly, it is preferable to prevent the occurrence of PCO rather than attempting to treat it at a later date through the application of laser energy.

Various procedures for the prevention of PCO have been suggested in recent years. Many such procedures have included the application of chemicals to the interior surface of the lens capsule in order to destroy residual lens epithelial cells. However, none of these procedures has proven to be particularly successful in the prevention of PCO due to the fact that it is extremely difficult to destroy residual lens epithelial cells without simultaneously destroying other cells within the eye, including the possible destruction of the corneal endothelium. Selective destruction of residual lens epithelial cells thus appears to be the key to the prevention of PCO.

Antimetabolites such as 5FU and daunomycin have been injected into the lens capsule of eyes in an attempt to prevent PCO. However, for antimetabolite therapy to be effective, the agents must be present when the epithelial cell proliferation resumes. Sustained drug delivery systems have also been investigated as a means for preventing PCO. However, the effective time frame within which to apply these agents may be difficult to determine. PCO is believed to result primarily from the propagation of lens epithelial cells of the germinal layer. These cells eventually proliferate and migrate across the lens capsule into the optical zone. The timing of such an event is difficult to accurately target for treatment thereof.

Immunotoxins which are hybrid molecules composed of monoclonal antibodies chemically linked to toxic moieties, have also been used in the selective destruction of residual lens epithelial cells. The monoclonal antibody directs the toxic moiety to the target cell. The cell then internalizes the immunotoxin, thereby causing the vital biological processes of the cell to be compromised by the toxic moiety. Other efforts have been made to destroy residual lens epithelial cells. One such effort included the use of a fibroblastic growth factor bonded to a toxic moiety. However, monoclonal antibodies and fibroblastic growth factors are relatively expensive and difficult to produce on a reliable and consistent basis. Therefore, it is desirable to employ a method that provides selective destruction of residual lens epithelial cells without the costs and problems associated with monoclonal antibodies and growth factors.

Accordingly, a long felt need exists for a reliable and cost effective method of preventing posterior cellular opacification or secondary cataracts in cataract patients having IOL implants.

BRIEF SUMMARY OF THE INVENTION

Posterior cellular opacification (PCO) is believed to result primarily from lens epithelial cells of the germinal layer. These cells eventually proliferate and migrate across the lens capsule into the optical zone. The surface treated intraocular lens (IOL) implant of the present invention delivers a cytotoxin to the lens capsule where it will remain until cellular migration across the lens capsule and the IOL implant occurs. Migrating cells ingest the toxin chemically bound to the IOL implant resulting in their destruction.

The surface treated IOL implant of the present invention is an IOL implant having a carbohydrate coating covalently bonded thereto. The carbohydrate coating is then non-covalently bonded to a protein or a polypeptide and toxin conjugate. Since the carbohydrate covalently bound to the IOL implant is the same or similar to carbohydrates present naturally in the lens capsule of the eye, binding affinities for the toxin are the same or similar between that of the IOL implant surface and that of the lens capsule. Once the surface treated IOL implant is in contact with the lens capsule, the toxin conjugate may bind to the tissue of the lens capsule. The present surface treated IOL implant as just described is used as customary in the field of ophthalmology for the replacement of a natural diseased lens such as in the case of a cataractous lens.

Accordingly, it is an object of the present invention to provide a surface treated IOL implant useful in the prevention of PCO.

Another object of the present invention is to provide a surface treated IOL implant useful in the prevention of PCO, which is reliable and cost effective.

Another object of the present invention is to provide a chemically bound surface treatment for the prevention of PCO, which is effective on IOL implants manufactured from any one of a variety of materials.

Another object of the present invention is to provide a method of using a surface treated IOL implant to prevent PCO.

Another object of the present invention is to provide a surface treated IOL implant effective in destroying residual lens epithelial cells in an eye.

Still another object of the present invention is to provide a surface treated IOL implant, which specifically destroys residual lens epithelial cells in an eye.

These and other objectives and advantages of the present invention, some of which are specifically described and others that are not, will become apparent from the detailed description, examples and claims that follow.

DETAILED DESCRIPTION OF THE INVENTION

The surface treated intraocular lens (IOL) implant of the present invention is intended to be implanted in an eye following extracapsular cataract extraction to destroy residual lens epithelial cells disposed on the interior surfaces of the lens capsule. By destroying the residual lens epithelial cells disposed on the interior surface of the lens capsule, the cells are prevented from proliferating and/or migrating along or across the surface of the lens capsule thereby preventing opacification of the optical zone commonly referred to as posterior capsular opacification (PCO). The IOL implant of the present invention may be employed in connection with any extracapsular cataract extraction procedure.

Extracapsular cataract extraction entails the formation of an incision through the eye in order to provide direct access to the anterior chamber of the eye. Although the necessary incision is usually formed at the limbus of the eye, it will be appreciated that alternative locations for this incision can be selected at the discretion of the surgeon. Following the formation of the incision, a cutting instrument is introduced though the incision into the anterior chamber of the eye. The cutting instrument is then advanced though the anterior chamber such that the cutting surface thereof is in the posterior chamber and in direct contact with the anterior surface of the lens capsule. A capsularhexis procedure is then performed, wherein a portion of the anterior membrane of the lens capsule is excised in order to provide direct access to the cataractous lens. The cataractous lens is then removed from the lens capsule. It will be appreciated that a variety of procedures can be used to remove the cataractous lens, including phacoemulsification and laser ablation. Upon removal of the cataractous lens from the lens capsule, an artificial IOL implant is inserted into the eye for the purpose of mimicking the refractive characteristics of the natural lens. IOL implants often are placed within the remaining portions of the lens capsule.

The surface treated IOL implant of the present invention may be manufactured in any form acceptable for the intended purpose of replacing a cataracts natural lens as known to those skilled in the art. The lens may be formed in a plate-style configuration as described in U.S. Pat. Nos. 4,664,666 and 4,936,850 each incorporated herein in its entirety by reference, or formed in a haptic-style configuration as described in U.S. Pat. Nos. 4,822,358, 4,842,600 and 4,863,464 each incorporated herein in its entirety by reference. However, although either lens configuration is equally suitable for the present invention, a haptic-style configuration is preferred for ease of placement in the eye.

The IOL implant of the present invention may be formed from any acceptable material known to those skilled in the art such as polymethylmethacrylate (PMMA), silicone, acrylates, hydrogels or a combination thereof. However, hydrogel material is preferred for use in the present invention due to the flexibility thereof.

Once the IOL implant is formed from a suitable material, the same is covalently bound with one or more but preferably one carbohydrate or glycosaminoglycan isolated from a proteoglycan such as for example but not limited to heparin, heparan sulfate and chondroitin sulfate, but preferably chondroitin sulfate due to its ready availability, or a synthetic equivalent of heparin such as for example but not limited to dextran sulfate. In the interest of simplicity, the term "carbohydrate" is used herein to refer to both glycosaminoglycans and synthetic equivalents thereto. In accordance with the present invention a carbohydrate, but preferably chondroitin sulfate, is covalently bound to the surface of the IOL implant using a crosslinker. In the case of carbohydrates isolated from proteoglycans, one or more but preferably one amine reactive crosslinker such as for example but not limited to (N-5-azido-2-nitrobenzoyloxysuccinimide) (ANB-NOS) is used. Carbohydrates isolated from proteoglycans contain a protein residue that readily reacts with amine reactive crosslinkers to bind the carbohydrate to the surface of the IOL implant. ANB-NOS contains a hydrazide group that readily reacts with amines, and a nitrophenyl azide group that reacts with the suitable IOL implant materials noted above upon activation with light.

Other suitable crosslinking agents which may be used to bind one or more but preferably one carbohydrate to the surface of an IOL implant include for example but are not limited to (bis-[beta-(4-azidosalicylamido)ethyl]disulfide)

(BASED), (N-hydroxysuccinimidyl-4-azidosalicylic acid) (NHS-ASA), (4-[p-azidosalicylamido]butylamine) (ASBA), (1-ethyl-3-[3dimethylaminopropyl] carbodiimide hydrochloride) (EDC), and sulfosuccinimidyl (4-[azidosalicylamido] hexanoate) (sulfo-NHS-LC-ASA). BASED has nonspecific binding activity and reacts with both hydrophobic groups, as present in the suitable IOL implant materials noted above, and carbohydrates which do not have amino groups such as for example dextran sulfate. BASED is also useful to react with carbohydrates that have amine groups. NHS-ASA and sulfo-NHS-LC-ASA are also photoreactive crosslinking agents suitable for use in the present invention. NHS-ASA and sulfo-NHS-LC-ASA each has hydroxyphenyl azide and ester reactive groups that react with amine groups. Such photoreactive crosslinking agents are useful in binding carbohydrates to hydrogel materials having a high water content. With such agents, coupling first takes place with the amine groups. After such coupling with the amine groups and upon exposure to a particular wavelength of light the photoreactive crosslinking agents react with the hydrophobic groups present on the hydrogel material. Another crosslinking agent suitable for use in the present invention with carbohydrates lacking a protein residue is (4-[p-azidosalicylamido]butylamine) (ASBA). ASBA reacts with carboxyl groups in the presence of a dehydrating agent such as EDC. ASBA also contains a photoreactive group that facilitates binding to the surface of the suitable IOL implant materials noted above. ASBA is useful in binding carboxyl groups which makes it ideal for binding carbohydrates with or without protein residues.

Suitable carbohydrate binding agents for use in accordance with the present invention include for example but are not limited to poly-L-lysine and poly-D-lysine, but preferably poly-L-lysine due to its ready availability and relatively low cost. For purposes of simplicity, each poly-L-lysine and poly-D-lysine is hereinafter referred to indiscriminately as "polylysine". Other suitable carbohydrate binding agents include but are not limited to fibronectin, laminin, type I, II, III and IV collagen, thrombospondin, vitronectin, polyarginine and platelet factor IV. In accordance with the present invention one or more but preferably one for purposes of simplicity suitable carbohydrate binding agent is conjugated with one or more but preferably one for purposes of simplicity cytotoxic agent. Suitable cytotoxic agents include ribosomal inhibitory proteins such as for example but not limited to saporin and ricin. Ribosomal inhibitory proteins are preferable in the present invention due to the fact that such proteins contain more inhibitory activity per microgram than other cytotoxic agents that can be used in connection with the method of the present invention. Other cytotoxic agents believed to be efficacious when used in connection with the present invention include, but are not limited to, antimitotic drugs such as methotrexate, 5-fluorouracil, daunomycin, doxorubicin, mitoxanthrone, vinca alkaloids, vinblastine, colchicine, and cytochasins, and ionophores such as monensin and ouabain.

A variety of known methods can be employed for conjugating the cytotoxic agent, most preferably saporin, to the carbohydrate binding agent, most preferably polylysine. For example, the carboxyl groups of the cytotoxic agent can be bonded to the amines of the carbohydrate binding agent using a water-soluble carbodiimide technique. When this technique for conjugation is used, the entire conjugate will be internalized by the residual lens epithelial cells and degraded by the cell to release the cytotoxic agent.

Hetero-bi-functional cross-linkers such as (N-succinimidyl 3-[2-pyridyldithio]propionate (SPDP) also can be used to conjugate the cytotoxic agent to the carbohydrate binding agent, thereby creating a disulfide bond between the cytotoxic agent and the carbohydrate binding agent. By way of example and not by way of limitation, a conjugate of polylysine and saporin was prepared by coupling polylysine to SPDP as described in more detail in the Examples below. The free SPDP was then removed using filtration technique or, in the alternative, through the use of a sepharose heparin column. The resulting polylysine-SPDP was then reduced with dithiothreitol. Saporin was then coupled with SPDP in the same manner and added to the solution of polylysine-SPDP. The resulting solution filtered to remove uncoupled agents, thereby producing a conjugated polylysine-saporin solution.

An IOL having a carbohydrate covalently bound to the surface thereof is then exposed to the conjugated carbohydrate binding agent-cytotoxic agent solution. The conjugated carbohydrate binding agent-cytotoxic agent thereby becomes chemically bound to the carbohydrate covalently bound to the surface of the IOL implant. The preferred method of making the subject IOL implant for the prevention of PCO is described in still greater detail in the Examples which follow.

EXAMPLES

Example 1

Binding of Carbohydrates to the Surface of an IOL Implant.

Described in detail below are preferred methods for binding heparin, heparan sulfate, chondroitin, chondroitin sulfate, dextrin and dextran sulfate to the surface of PMMA, hydrogel, acrylate or silicone IOL implants. Heparin, heparan sulfate, chondroitin sulfate and dextran sulfate can each be obtained from Sigma Chemical Company, St. Louis, Missouri. The crosslinkers ANB-NOS, NHS-ASA, sulfo-NHS-LC-ASA, ASBA, EDC, and BASED may all be obtained from Pierce Chemical Company, Rockford, Ill.

As described above, ANB-NOS, NHS-ASA and sulfo-NHS-LC-ASA are suitable for coupling heparin, heparan sulfate and chondroitin sulfate to the suitable IOL implant materials as these carbohydrates are derived from proteoglycans and contain a protein residue. ASBA reacts with carboxyl groups present on each of the carbohydrates noted. BASED has nonspecific-binding activity resulting from photo-activation of a phenyl azide group that allows it to react with each of the carbohydrates noted. Each of the crosslinkers noted herein utilizes nonspecific binding activity resulting from photo-activation of a phenyl azide group to bind to the IOL implant material surface. For that reason, this coupling mechanism is the same regardless of the suitable IOL implant material chosen for use.

A. Binding of Heparin or Heparan Sulfate to PMMA, Hydrogel, Acrylate or Silicone IOL Implant.

Heparin or heparan sulfate may be bound to a PMMA, hydrogel, acrylate or silicone IOL implant using the crosslinker ANB-NOS. Heparin or heparan sulfate derived from hog intestines (Sigma Chemical Company, St. Louis, Mo.) is dissolved in a 50 mm phosphate buffer (pH 7) at 5 mg/ml. In the dark, ANB-NOS is solubilized in DMSO at the highest concentration practical. ANB-NOS is then added to the heparin or heparan sulfate solution in a 20 fold molar excess. Unreacted ANB-NOS is removed by dialysis. A PMMA, hydrogel, acrylate or silicone IOL implant is then submerged in enough of the solution to cover all surfaces. High intensity light such as a camera flash bulb flash that includes light within the range of 320 to 350 nm is then applied to activate the nitrophenyl azide groups and bind heparin or heparan sulfate to the IOL implant surface. Light should be applied to all surfaces of the IOL implant to ensure complete coating thereof. The IOL implant is then washed in distilled water to remove any unbound molecules.

B. Binding of Chondroitin Sulfate, Heparin or Heparan Sulfate to PMMA, Hydrogel, Acrylate or Silicone IOL Implant.

The following solutions are prepared in the dark.

100 ul of a 50 mM solution of ANB-NOS in phosphate buffered saline (PBS)

900 ul of a 10 mg/ml solution of chondroitin sulfate, heparin or heparan sulfate in PBS The solutions are then combined and allowed to react at room temperature for two hours. After the two hours, the non-coupled products are removed by dialysis or gel filtration. After removing the non-coupled products, a PMMA, hydrogel, acrylate or silicone IOL implant is submerged in the reaction mixture and incubated for fifteen minutes at 37 degrees Celsius. After incubation, the phenyl azide group is activated with several camera flash bulb flashes. Following the flashes, the IOL implant is washed with PBS to remove any unreacted products.

C. Binding of Chondroitin Sulfate, Heparin or Heparan Sulfate to PMMA, Hydrogel, Acrylate or Silicone IOL Implant The following solutions are prepared in the dark.

400 ul of a 0.5 mM solution of NHS-ASA or sulfo-NHS-LC-ASA in PBS 600 ul of a 10 mg/ml solution of chondroitin sulfate, heparin or heparan sulfate in PBS The solutions are then combined and allowed to react at room temperature for one hour. After the hour, the non-coupled products are removed by dialysis or gel filtration. After removing the non-coupled products, a PMMA, hydrogel, acrylate or silicone IOL implant is submerged in the reaction mixture and incubated for fifteen minutes at 37 degrees Celsius. After incubation, the reaction mixture is irradiated with long-wave ultraviolet light for ten minutes or approximately five camera flash bulb flashes. Following the irradiation or flashes, the IOL implant is washed with PBS to remove any unreacted products.

D. Binding of Dextran Sulfate, Chondroitin Sulfate, Heparln or Heparan Sulfate to PMMA, Hydrogel, Acrylate or Silicone IOL Implant.

The following solutions are prepared in the dark.

110 ul of 5 mM ASBA in PBS 1 ml of 10 mg/ml dextran sulfate, chondroitin sulfate, heparin or heparan sulfate in (2-[N-morpholino] ethanesulfonic acid) (MES) buffer (pH 4.5)

20 ul of 5 mg/ml EDC in MES buffer (pH 4.5)

The solutions are then combined and incubated at room temperature for two hours. After the two hours, the non-coupled products are removed by dialysis or gel filtration. After removing the non-coupled products, a PMMA, hydrogel, acrylate or silicone IOL implant is submerged in the reaction mixture and incubated for fifteen minutes at 37 degrees Celsius. After incubation, the photoactive groups within the reaction mixture are activated by several camera flash bulb flashes. Following the irradiation or flashes, the IOL implant is washed with PBS to remove any unreacted products.

E. Binding of Dextran Sulfate, Chondroitin Sulfate, Hepadn or Heparan Sulfate to PMMA, Hydrogel, Acrylate or Silicone IOL Implant The following solutions are prepared in the dark.

10 ul of 60 mg/ml BASED dissolved in dimethylsulfoxide (DMSO)

1 ml of PBS containing 10 mg/ml dextran sulfate

The solutions are then combined with an IOL implant placed therein and incubated at room temperature for fifteen minutes. After incubation, the photoactive groups within the reaction mixture are activated by exposing the same to 366 nm light for fifteen minutes. Following the exposure to light, the IOL implant is washed with PBS to remove any unreacted products.

Example 2

Conjugation of Polylysine-Saporin

Saporin was conjugated to polylysine using (N-succinimidyl 3-[2-pyridyldithio]propionate (SPDP) according to instructions provided by Pierce Chemical Company, Rockford, Ill. SPDP in 1.5 M excess was allowed to react with saporin and polylysine individually to generate sulfhydryl groups on each component. Polylysine-SPDP was then treated with dithiothreitol and allowed to react with saporin-SPDP resulting in a disulfide linkage between the two species. The molar ratio of saporin to polylysine in the conjugate was calculated to be 1:1. The polylysine-saporin conjugate (PLS) was isolated from the free components by heparin sepharose chromatography. Molecular weight analysis was performed using sodium dodecyl sulfate-polyacrylamide gel electrophoresis (SDS-PAGE). As expected, there was an apparent increase in molecular weight after conjugation to polylysine. Under non-reducing conditions PLS migrates as 2 bands with estimated molecular weights of 43,000 and 66,000 kD. The lower molecular weight band represents a conjugate of 1 polylysine +1 saporin molecule and the higher molecular weight band represents a conjugate of 1 polylysine +2 saporin molecules. In support of this, when PLS is run under reducing conditions, only one band results which migrates with free saporin. Polylysine is not visible with Coomassie blue staining. PLS was quantitated using the Lowry method for protein determination.

Example 3

Binding of Polylysine-Saporin Conjugate to Carbohydrate Bound IOL Implant

Polylysine-saporin (PLS) is applied to any of the carbohydrate coated IOL implants produced through the methods provided in Example 1 above by submerging the IOL implant into 1 ml PBS or balanced salt solution (BSS) containing 25–200 ug PLS for approximately fifteen minutes. After submersion, the IOL is removed from the PBS/PLS or BSS/PLS solution and washed with PBS or BSS to remove any excess or residual PLS.

The subject IOL implant manufactured in accordance with the methods described in detail in the above Examples is useful to prevent PCO when implanted in an eye to replace a cataracts natural lens. Such surgical method of implanting an IOL implant in an eye to replace a cataracts natural lens is well known to those skilled in the art as described in U.S. Pat. Nos. 4,955,889 and 4,957,505 each incorporated herein in its entirety by reference.

As described above, the surface treated IOL implant of the present invention provides an effective method of preventing PCO in cataract patients. The present description of the subject IOL implant, the method of making the same and the method of using the same is provided for purposes of illustration and explanation. It will be apparent to those skilled in the art that modifications and changes may be made to the preferred embodiment described herein without departing from its scope and spirit.

I claim:

1. An intraocular lens implant comprising:
   an intraocular lens implant;
   a carbohydrate bound to the surface of the implant; and
   a carbohydrate binding agent conjugated with a cytotoxic agent bound to said carbohydrate.

2. The intraocular lens implant of claim 1 wherein said implant is manufactured from one or more materials selected from the group consisting of polymethylmethacrylate, silicone, acrylate and hydrogel.

3. The intraocular lens implant of claim 1 wherein said implant is manufactured from a hydrogel material.

4. The intraocular lens implant of claim 1 wherein said implant is manufactured in a plate configuration or a haptic configuration.

5. The intraocular lens implant of claim 1 wherein said carbohydrate is selected from the group consisting of heparin, heparan sulfate, chondroitin, chondroitin sulfate, dextrin and dextran sulfate.

6. The intraocular lens implant of claim 1 wherein said carbohydrate is heparin.

7. The intraocular lens implant of claim 1 wherein said carbohydrate is chondroitin.

8. The intraocular lens implant of claim 1 wherein said carbohydrate is bound to the surface of the implant using a crosslinking agent.

9. The intraocular lens implant of claim 1 wherein said carbohydrate is bound to the surface of the implant using a crosslinking agent selected from the group consisting of (4-[p-azidosalicylamido]butylamine), (bis-[beta-(4-azidosalicylamido)ethyl]disulfide), (N-5-azido-2-nitrobenzoyloxysuccinimide), (1-ethyl-3-[3-dimethylaminopropyl] carbodiimide hydrochloride), sulfosuccinimidyl (4-[azidosalicylamido] hexanoate) and (N-hydroxysuccinimidyl-4-azidosalicylic acid).

10. The intraocular lens implant of claim 1 wherein said carbohydrate is bound to the surface of the implant using (N-5-azido-2-nitrobenzoyloxysuccinimide).

11. The intraocular lens implant of claim 1 wherein said carbohydrate binding agent is selected from the group consisting of poly-L-lysine, poly-D-lysine, fibronectin, laminin, type I, II, III or IV collagen, thrombospondin, vitronectin, polyarginine and platelet factor IV.

12. The intraocular lens implant of claim 1 wherein said carbohydrate binding agent is poly-L-lysine or poly-D-lysine.

13. The intraocular lens implant of claim 1 wherein said cytotoxic agent is selected from the group consisting of ribosomal inhibitory proteins, antimitotic drugs and ionophores.

14. The intraocular lens implant of claim 1 wherein said cytotoxic agent is a ribosomal inhibitory protein.

15. The intraocular lens implant of claim 1 wherein said cytotoxic agent is selected from the group consisting of saporin, ricin, methotrexate, 5-fluorouracil, daunomycin, doxorubicin, mitoxanthrone, vinca alkaloids, vinblastine, colchicine, cytochasins, monensin and ouabain.

16. The intraocular lens implant of claim 1 wherein said cytotoxic agent is saporin.

17. The intraocular lens implant of claim 1 wherein said carbohydrate binding agent is conjugated to said cytotoxic agent using (N-succinimidyl 3-[2-pyridyldithio]propionate).

18. A method of manufacturing an intraocular lens implant comprising:
    fabricating an intraocular lens implant;
    binding one or more carbohydrates to the surface of the implant;
    conjugating a carbohydrate binding agent with a cytotoxic agent to form conjugated agents; and
    exposing the intraocular implant to the conjugated agents thereby allowing the conjugated agents to bind with the carbohydrates.

19. The method of claim 18 wherein said implant is manufactured from one or more materials selected from the group consisting of polymethylmethacrylate, silicone, acrylate and hydrogel.

20. The method of claim 18 wherein said implant is manufactured from a hydrogel material.

21. The method of claim 18 wherein said implant is manufactured in a plate configuration or a haptic configuration.

22. The method of claim 18 wherein said carbohydrate is selected from the group consisting of heparin, heparan sulfate, chondroitin, chondroitin sulfate, dextrin and dextran sulfate.

23. The method of claim 18 wherein said carbohydrate is heparin.

24. The method of claim 18 wherein said carbohydrate is chondroitin.

25. The method of claim 18 wherein said carbohydrate is bound to the surface of the implant using a crosslinking agent.

26. The method of claim 18 wherein said carbohydrate is bound to the surface of the implant using a crosslinking agent selected from the group consisting of (4-[p-azidosalicylamido]butylamine), (bis-[beta-(4-azidosalicylamido)ethyl]disulfide), (N-5-azido-2-nitrobenzoyloxysuccinimide), (1-ethyl-3-[3-dimethylaminopropyl] carbodiimide hydrochloride), sulfosuccinimidyl (4-[azidosalicylamido] hexanoate) and (N-hydroxysuccinimidyl-4-azidosalicylic acid).

27. The method of claim 18 wherein said carbohydrate is bound to the surface of the implant using (N-5-azido-2-nitrobenzoyloxysuccinimide).

28. The method of claim 18 wherein said carbohydrate binding agent is selected from the group consisting of poly-L-lysine, poly-D-lysine, fibronectin, laminin, type I, II, III or IV collagen, thrombospondin, vitronectin, polyarginine and platelet factor IV.

29. The method of claim 18 wherein said carbohydrate binding agent is poly-L-lysine or poly-D-lysine.

30. The method of claim 18 wherein said cytotoxic agent is selected from the group consisting of ribosomal inhibitory proteins, antimitotic drugs and ionophores.

31. The method of claim 18 wherein said cytotoxic agent is a ribosomal inhibitory protein.

32. The method of claim 18 wherein said cytotoxic agent is selected from the group consisting of saporin, ricin, methotrexate, 5-fluorouracil, daunomycin, doxorubicin, mitoxanthrone, vinca alkaloids, vinblastine, colchicine, cytochasins, monensin and ouabain.

33. The method of claim 18 wherein said cytotoxic agent is saporin.

34. The method of claim 18 wherein said carbohydrate binding agent is conjugated to said cytotoxic agent using (N-succinimidyl 3-[2-pyridyldithio]propionate).

35. A method of implanting an intraocular lens implant within an eye comprising:
    creating an incision in an eye;

implanting said implant bound with a carbohydrate, a carbohydrate binding agent and a cytotoxic agent within the incision in the eye; and closing said incision.

36. The method of claim 35 wherein said implant is manufactured from one or more materials selected from the group consisting of polymethylmethacrylate, silicone, acrylate and hydrogel.

37. The method of claim 35 wherein said implant is manufactured from a hydrogel material.

38. The method of claim 35 wherein said implant is manufactured in a plate configuration or a haptic configuration.

39. The method of claim 35 wherein said carbohydrate is selected from the group consisting of heparin, heparan sulfate, chondroitin, chondroitin sulfate, dextrin and dextran sulfate.

40. The method of claim 35 wherein said carbohydrate is heparin.

41. The method of claim 35 wherein said carbohydrate is chondroitin.

42. The method of claim 35 wherein said carbohydrate is bound to the surface of the implant using a crosslinking agent.

43. The method of claim 35 wherein said carbohydrate is bound to the surface of the implant using a crosslinking agent selected from the group consisting of (4-[p-azidosalicylamido]butylamine), (bis-[beta-(4-azidosalicylamido)ethyl]disulfide), (N-5-azido-2-nitrobenzoyloxysuccinimide), (1-ethyl-3-[3-dimethylaminopropyl] carbodiimide hydrochloride), sulfosuccinimidyl (4-[azidosalicylamido] hexanoate) and (N-hydroxysuccinimidyl-4-azidosalicylic acid).

44. The method of claim 35 wherein said carbohydrate is bound to the surface of the implant using (N-5-azido-2-nitrobenzoyloxysuccinimide).

45. The method of claim 35 wherein said carbohydrate binding agent is selected from the group consisting of poly-L-lysine, poly-D-lysine, fibronectin, laminin, type I, II, III or IV collagen, thrombospondin, vitronectin, polyarginine and platelet factor IV.

46. The method of claim 35 wherein said carbohydrate binding agent is poly-L-lysine or poly-D-lysine.

47. The method of claim 35 wherein said cytotoxic agent is selected from the group consisting of ribosomal inhibitory proteins, antimitotic drugs and ionophores.

48. The method of claim 35 wherein said cytotoxic agent is a ribosomal inhibitory protein.

49. The method of claim 35 wherein said cytotoxic agent is selected from the group consisting of saporin, ricin, methotrexate, 5-fluorouracil, daunomycin, doxorubicin, mitoxanthrone, vinca alkaloids, vinblastine, colchicine, cytochasins, monensin and ouabain.

50. The method of claim 35 wherein said cytotoxic agent is saporin.

51. The method of claim 35 wherein said carbohydrate binding agent is conjugated to said cytotoxic agent using (N-succinimidyl 3-[2-pyridyldithio]propionate).

* * * * *